(12) United States Patent
Spayd et al.

(10) Patent No.: US 9,284,552 B2
(45) Date of Patent: Mar. 15, 2016

(54) MODIFIED CELL LINES FOR INCREASING LENTIVIRAL TITERS

(71) Applicants: Katie Jansen Spayd, Huntsville, AL (US); Jon Karpilow, Boulder, CO (US); John K. Wakefield, Birmingham, AL (US)

(72) Inventors: Katie Jansen Spayd, Huntsville, AL (US); Jon Karpilow, Boulder, CO (US); John K. Wakefield, Birmingham, AL (US)

(73) Assignee: GE Healthcare Dharmacon, Inc., Lafayette, CO (US)

( * ) Notice: Subject to any disclaimer, the term of this patent is extended or adjusted under 35 U.S.C. 154(b) by 309 days.

(21) Appl. No.: 13/854,995

(22) Filed: Apr. 2, 2013

(65) Prior Publication Data
US 2013/0217121 A1    Aug. 22, 2013

Related U.S. Application Data

(62) Division of application No. 13/222,509, filed on Aug. 31, 2011, now abandoned.

(60) Provisional application No. 61/388,338, filed on Sep. 30, 2010.

(51) Int. Cl.
| | | |
|---|---|---|
| C12N 7/01 | (2006.01) |
| C12N 7/02 | (2006.01) |
| C12N 15/86 | (2006.01) |
| A61K 39/21 | (2006.01) |
| C12N 15/113 | (2010.01) |

(52) U.S. Cl.
CPC .............. *C12N 15/113* (2013.01); *C12N 15/86* (2013.01); *C12N 2740/15051* (2013.01); *C12N 2740/15052* (2013.01)

(58) Field of Classification Search
None
See application file for complete search history.

(56) References Cited

U.S. PATENT DOCUMENTS

| | | | |
|---|---|---|---|
| 5,994,136 A * | 11/1999 | Naldini et al. ................ 435/455 |
| 7,132,239 B2 | 11/2006 | Livak et al. |
| 7,595,387 B2 | 9/2009 | Leake et al. |
| 7,691,995 B2 | 4/2010 | Zamore et al. |
| 2005/0255487 A1 | 11/2005 | Khvorova |
| 2012/0083035 A1 | 4/2012 | Spayd |

OTHER PUBLICATIONS

Neal et al (Nature 451: 425-430).*
Poluri et al (Mol. Ther. 16(2): 378-386, 2008).*
Carter et al (Trends in Microbiology 10(5): 203-205, May 2002).*
Goila-Gaur et al (Journal of Virology, 77(11): 6507-6519, 2003).*
Harrist et al (PLoS One 4(3):e5020, Mar. 2009).*
Chable-Bessia et al, Retrovirology, 2009, 6:26.
Ansorge et al, J. Gene Med, 2009, 11: 868-876.

* cited by examiner

*Primary Examiner* — Richard Schnizer
(74) *Attorney, Agent, or Firm* — Dorf & Nelson LLP; Scott D. Locke, Esq.

(57) ABSTRACT

The present disclosure provides a method of modifying cells in order to enhance lentiviral titers, cell lines that are modified and modifying reagents. By mediating individual genes and combination thereof, lentiviral titers may be increased.

19 Claims, 7 Drawing Sheets

SEQUENCE LISTING

<160> NUMBER OF SEQ ID NOS: 20

<210> SEQ ID NO 1
<211> LENGTH: 19
<212> TYPE: RNA
<213> ORGANISM: Artificial sequence
<220> FEATURE:
<223> OTHER INFORMATION: Synthetic

<400> SEQUENCE: 1
gaagcucgau gaagauuua                                        19

<210> SEQ ID NO 2
<211> LENGTH: 19
<212> TYPE: RNA
<213> ORGANISM: Artificial sequence
<220> FEATURE:
<223> OTHER INFORMATION: Synthetic

<400> SEQUENCE: 2
ggaauuauau gacuggaau                                        19

<210> SEQ ID NO 3
<211> LENGTH: 19
<212> TYPE: RNA
<213> ORGANISM: Artificial sequence
<220> FEATURE:
<223> OTHER INFORMATION: Synthetic

<400> SEQUENCE: 3
gcaagacgca caggaauua                                        19

<210> SEQ ID NO 4
<211> LENGTH: 19
<212> TYPE: RNA
<213> ORGANISM: Artificial sequence
<220> FEATURE:
<223> OTHER INFORMATION: Synthetic

<400> SEQUENCE: 4
caacauagac uacacgauu                                        19

<210> SEQ ID NO 5
<211> LENGTH: 19
<212> TYPE: RNA
<213> ORGANISM: Artificial sequence
<220> FEATURE:
<223> OTHER INFORMATION: Synthetic

<400> SEQUENCE: 5
uaaaguagcu ggaaugaug                                        19

<210> SEQ ID NO 6
<211> LENGTH: 19
<212> TYPE: RNA
<213> ORGANISM: Artificial sequence
<220> FEATURE:
<223> OTHER INFORMATION: Synthetic

<400> SEQUENCE: 6
ggaagaggcu gacuaugaa                                        19

<210> SEQ ID NO 7
<211> LENGTH: 19
<212> TYPE: RNA
<213> ORGANISM: Artificial sequence

```
<220> FEATURE:
<223> OTHER INFORMATION: Synthetic

<400> SEQUENCE: 7
gaauaucgau ccuauguuc                                                    19

<210> SEQ ID NO 8
<211> LENGTH: 19
<212> TYPE: RNA
<213> ORGANISM: Artificial sequence
<220> FEATURE:
<223> OTHER INFORMATION: Synthetic

<400> SEQUENCE: 8
gauccuaugu ucaaucuaa                                                    19

<210> SEQ ID NO 9
<211> LENGTH: 19
<212> TYPE: RNA
<213> ORGANISM: Artificial sequence
<220> FEATURE:
<223> OTHER INFORMATION: Synthetic

<400> SEQUENCE: 9
gaaagaagcc caagauguc                                                    19

<210> SEQ ID NO 10
<211> LENGTH: 19
<212> TYPE: RNA
<213> ORGANISM: Artificial sequence
<220> FEATURE:
<223> OTHER INFORMATION: Synthetic

<400> SEQUENCE: 10
gcuuaaggau guaaagauu                                                    19

<210> SEQ ID NO 11
<211> LENGTH: 19
<212> TYPE: RNA
<213> ORGANISM: Artificial sequence
<220> FEATURE:
<223> OTHER INFORMATION: Synthetic

<400> SEQUENCE: 11
ugacacgucu aucaaguuu                                                    19

<210> SEQ ID NO 12
<211> LENGTH: 19
<212> TYPE: RNA
<213> ORGANISM: Artificial sequence
<220> FEATURE:
<223> OTHER INFORMATION: Synthetic

<400> SEQUENCE: 12
gcaguuagcc ucacagaag                                                    19

<210> SEQ ID NO 13
<211> LENGTH: 19
<212> TYPE: RNA
<213> ORGANISM: Artificial sequence
<220> FEATURE:
<223> OTHER INFORMATION: Synthetic

<400> SEQUENCE: 13
gcacgucuuu ccagaauuc                                                    19
```

```
<210> SEQ ID NO 14
<211> LENGTH: 19
<212> TYPE: RNA
<213> ORGANISM: Artificial sequence
<220> FEATURE:
<223> OTHER INFORMATION: Synthetic

<400> SEQUENCE: 14
agagagcgau gccauguuu                                                   19

<210> SEQ ID NO 15
<211> LENGTH: 19
<212> TYPE: RNA
<213> ORGANISM: Artificial sequence
<220> FEATURE:
<223> OTHER INFORMATION: Synthetic

<400> SEQUENCE: 15
gauauucugu ggaaagugu                                                   19

<210> SEQ ID NO 16
<211> LENGTH: 19
<212> TYPE: RNA
<213> ORGANISM: Artificial sequence
<220> FEATURE:
<223> OTHER INFORMATION: Synthetic

<400> SEQUENCE: 16
guaaacgucc guaacaaga                                                   19

<210> SEQ ID NO 17
<211> LENGTH: 19
<212> TYPE: RNA
<213> ORGANISM: Artificial sequence
<220> FEATURE:
<223> OTHER INFORMATION: Synthetic

<400> SEQUENCE: 17
ggagagauca cuacauuaa                                                   19

<210> SEQ ID NO 18
<211> LENGTH: 19
<212> TYPE: RNA
<213> ORGANISM: Artificial sequence
<220> FEATURE:
<223> OTHER INFORMATION: Synthetic

<400> SEQUENCE: 18
gcagagugcc cauggaaga                                                   19

<210> SEQ ID NO 19
<211> LENGTH: 19
<212> TYPE: RNA
<213> ORGANISM: Artificial sequence
<220> FEATURE:
<223> OTHER INFORMATION: Synthetic

<400> SEQUENCE: 19
gaaucgcgga caagaagua                                                   19

<210> SEQ ID NO 20
<211> LENGTH: 19
<212> TYPE: RNA
<213> ORGANISM: Artificial sequence
<220> FEATURE:
<223> OTHER INFORMATION: Synthetic
```

```
<400> SEQUENCE: 20
ggauaggaau ucuggugcu                                            19
```

MODIFIED CELL LINES FOR INCREASING LENTIVIRAL TITERS

CROSS-REFERENCE TO RELATED APPLICATION

This application is a divisional of U.S. Ser. No. 13/222,509, filed Aug. 31, 2011, pending, which claims the benefit of the filing date of U.S. Provisional Application Ser. No. 61/388,338, filed Sep. 30, 2010, the entire disclosures of which are incorporated by reference as if set forth fully herein.

FIELD OF INVENTION

The present invention relates to lentiviruses

BACKGROUND OF INVENTION

Lentiviruses (LVs) designed to deliver transgenic cargo (e.g., a protein coding sequence or an shRNA) are valuable tools in basic research, bioproduction, and therapeutic delivery. In order to generate these valuable reagents, researchers generally introduce a transfer vector (encoding the desired transgenic viral genome to be packaged) along with one or more packaging vectors (that produce essential viral proteins) into an appropriate packaging cell line (e.g. HEK 293 cells). The inventors have recognized that the current set of reagents and protocols is highly inefficient and that new methods are needed to develop sufficient quantities of viral particles. For this reason, the following invention describes novel and non-obvious sets of reagents and processes for greatly enhancing LV production.

SUMMARY

The present invention provides modified packaging cell lines and methods for efficient production of lentiviral particles. Specifically, in some embodiments the cells have been altered in such a way as to knockout or knockdown one or more host encoded genes that negatively affect lentiviral vector particle formation in the packaging cell line. Alternatively or in addition to the aforementioned alterations, the cells have been modified to over-express one or more host encoded genes that facilitate viral particle formation and release. Host genes that can be targeted (for knockout or knockdown) to enhance LV particle formation and release include, but are not limited to, Dicer, Drosha, DGCR8, Hrs, and Tetherin. Host genes that can be over-expressed to enhance LV particle formation and release include, but are not limited to, Annexin2 and Tsg101. The present invention describes individual knockouts (or knockdowns) and enhancements, as well as combinations of knockouts (or knockdowns) and/or enhancements, as well as the effects that modulating these genes (singularly or in combination) have on viral production.

DETAILED DESCRIPTION OF THE EMBODIMENTS

The present disclosure will now be described in connection with preferred embodiments. These embodiments are presented to aid in an understanding of the present disclosure and are not intended, and should not be construed, to limit the disclosure in any way. All alternatives, modifications and equivalents that may become apparent to those of ordinary skill upon reading this disclosure are included within the spirit and scope of the present disclosure.

The present disclosure is directed to compositions and methods for generating lentiviral particles. Through the use of the present disclosure, modified cells and derivatives thereof may be constructed to enhance lentiviral production.

Figure 1A:
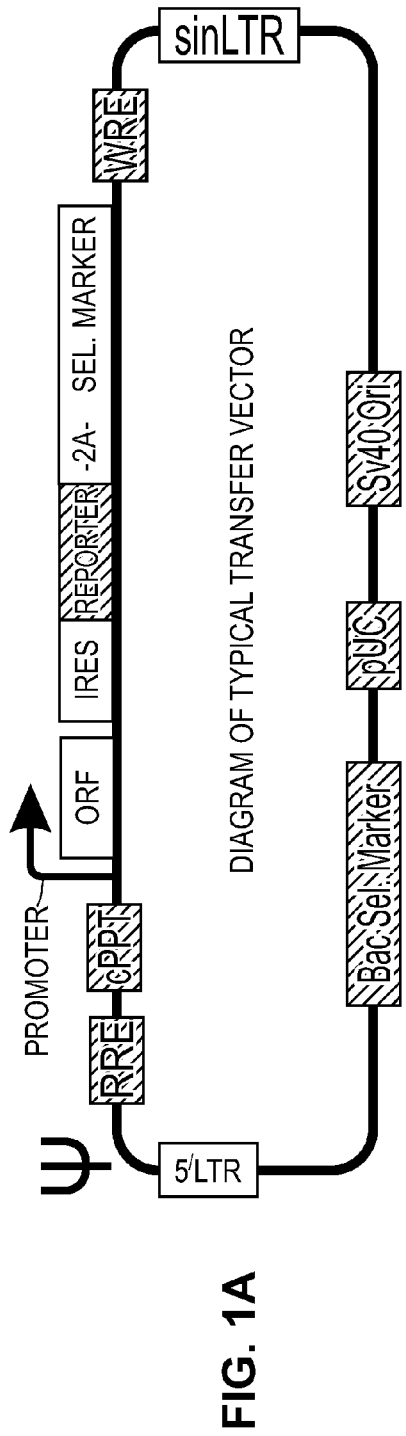
FIG. 1A shows a schematic of a typical lentiviral transfer vector, which includes for instance, an open reading frame (ORF), an IRES (internal ribosomal entry sequence) sequence for cap-independent translation, a reporter construct to identify cells that have been transduced, as well as a 2A peptide separating the reporter construct from a selectable marker (e.g. puromycin). Alternative designs that, for instance, drive the expression of an RNAi silencing reagent (e.g., an shRNA) are envisioned.
Figure 1B:
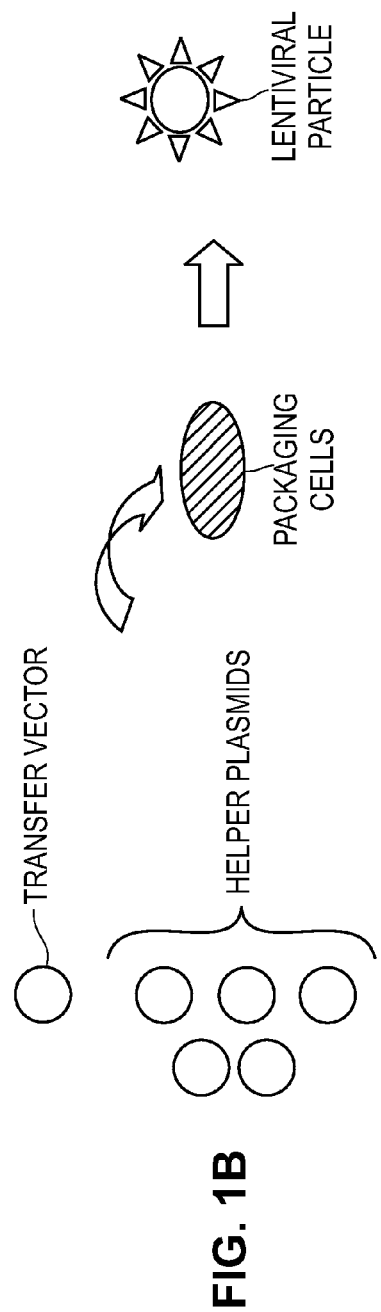
FIG. 1B is a simplified schematic of the steps involved in creating a lentiviral particle.
Figure 1C:
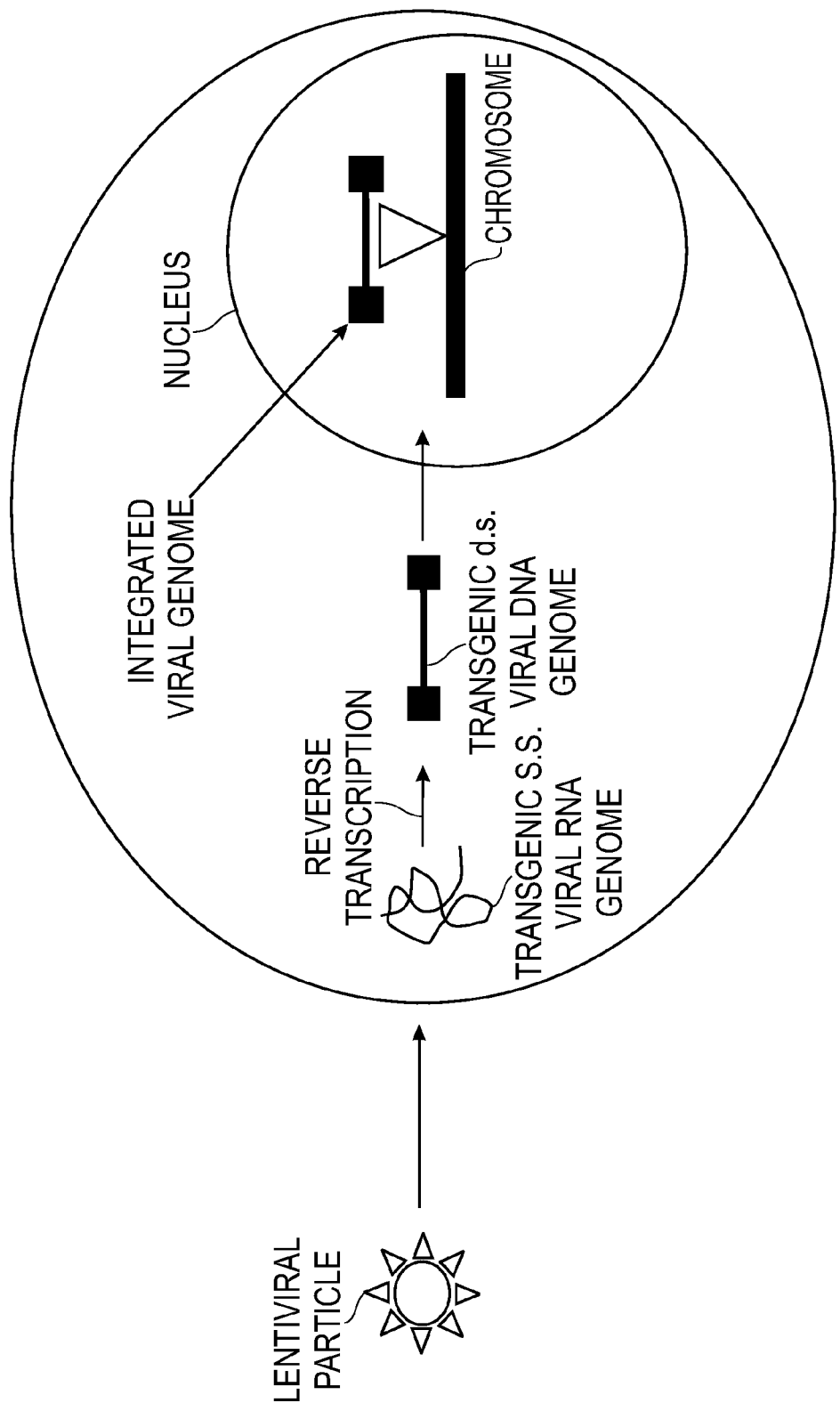
FIG. 1C is a simplified schematic of the lentiviral lifecycle including cellular entry, reverse transcription of the viral genome from RNA→DNA, transport into the nucleus, and integration into the host genome.

Lentiviruses can be used to transfer genetic material (e.g., protein coding genes, miRNAs, and shRNAs) into cells. To achieve this, a lentiviral transfer vector or plasmid comprising, consisting essentially of or consisting of DNA encoding the necessary elements for packaging into a lentiviral particle (see FIG. 1A) is transfected into cells along with helper vectors (see FIG. 1B). In the packaging cell, the information associated with the (DNA) transfer vector is transferred to a viral RNA genome, which is then packaged into a lentiviral particle that buds from the cell into the surrounding media. Lentiviral particles created by this method are then capable of infecting or "transducing" target cells (FIG. 1C). During the course of transduction, the information associated with the viral RNA genome is transferred into DNA that is then delivered to the nucleus where it is stably integrated into the host chromosome. In this fashion, long-term expression of the genetic payload can be achieved.

A critical parameter of lentiviral production is viral titer. In this instance, viral titer is defined as the number of infectious particles per volume, and lentiviral packaging protocols that produce higher titers greatly facilitate research and developmental studies. Historically, lentiviral titers are low ($10^4$-$10^7$ infectious viral particles per ml), and previous studies have identified several factors (including the size of the transfer vector, the method of introducing the transfer and packaging vectors into the packaging cells, and the ratio of transfer vectors to packaging vectors) that contribute to the viral titer. Still, even when all of these elements have been optimized, overall viral titers are still lower than those obtained with other viral production systems (e.g., adenovirus, >$10^{10}$ particles per ml).

In the course of the work presented here, the inventors have discovered that modulating the expression of a combination of host (cellular) genes strongly enhances lentiviral production. Specifically, modulation (which includes both up and down regulation of specific host genes) has been shown to increase overall viral titers by ten-fold or more. Thus, according to the first embodiment, the present disclosure is directed to a cell line in which a combination of host genes is modulated to enhance production of virus, or virus-like particles (VLPs) and a method of producing high viral titers using such cell line.

It should be noted that while many of the genes have been shown to alter viral titer, other sets of (host) genes may be modulated to enhance the infectivity of the resulting viral particles. Under these instances, the overall numbers of viral titers (per se) may not change, but the ability of a given particle to transduce a cell would increase. In some embodiments, the present invention is directed to cell lines, in which a first gene has been modulated to enhance production of viruses or virus-like particles, and a second gene has been modulated to enhance the infectivity of the resulting viral particle. In various embodiments, the present invention is also directed to methods for making or using these cell lines.

A variety of cells/cell types including primary cells or cells derived from a cell line can be used in the invention. In cases where the cells are derived from a cell line, the cell line can be a transgenic cell line specifically modified to produce e.g., LV particles. For instance, the cell line can represent a minimal packaging cell line that has been modified to express (in a constitutive or inducible manner) one or more of the following genes including (but not limited to) gag-pol, tat, or rev. In addition, the cells can be mammalian or non-mammalian in origin and be adherent or non-adherent in nature. Preferably, the cells of the invention are adherent cells. More preferably, the cells are derived from human embryonic kidney cells with examples of desired cells including but not limited to HEK-293 cells (ATCC No. CRL-1573) and HEK 293T cells (ATCC No CRL-11268). Other cell lines that can be used in the present invention are available from ATCC.

As stated above, the inventors have identified combinations of host-encoded genes that when modulated (i.e., up- or down-regulation of function) enhance lentiviral production. In the context of the invention, host-encoded gene products that inhibit LV production are genes that are targeted for suppression in order to enhance LV titers. Conversely, host-encoded gene products that facilitate LV production are genes whose function is bolstered to enhance LV titers. The host-encoded genes that can be modulated can include both protein encoding genes and non-protein encoding genes (e.g., miRNAs).

With respect to gene suppression, complete suppression of the target gene function is unnecessary to facilitate LV production, and as such, technologies that knockdown or knockout function are compatible with the invention. For this reason, there are a variety of technologies that can be employed to curb gene function. These include, but are not limited to, knockdown or knockout of the target gene at the genome-level (e.g., by zinc-finger-based technologies, transposon/insertion-based mutatgenesis), suppression of gene transcription (e.g., by epigenetic mechanisms), degradation and/or suppression of translation of the target transcript (e.g., via RNAi-based technologies), or suppression of protein function by any number of mechanisms including but not limited to altering post-translational modification patterns, exposure to a known modulator protein(s), a regulatory peptide, or a small molecule, that alters the function of the host target protein. In one preferred method, gene function is suppressed using RNAi technology. Under these conditions, knockdown can be transient (e.g., mediated by siRNA), constitutive (e.g., mediated by stable expression of an shRNA from a plasmid or integrated expression construct), or regulated (e.g., ligand-mediated shRNA expression). In cases where the strategy involves e.g., stable knockdown, the inventors envision the development of modified cell lines to achieve this goal. Described RNAi reagents can be delivered to cells by any number of mechanisms including, but not limited to, transfection (using lipids, peptide-based delivery reagents, or alike), mechanical methods (e.g., electroporation), passive delivery, or transduction.

RNAi can be accomplished in mammals by using siRNA. When using siRNA, one may, for example, use duplexes that have 18-30 bases pairs, 19-30 base pairs, 19-23 base pairs or 19 base pairs and either no overhangs or one or more overhangs at the 3' or 5' ends of the sense or antisense strands. Furthermore, the siRNA may be modified or unmodified. Examples of modifications include those described in U.S. Pat. No. 7,595,387, issued Sep. 29, 2009 and U.S. Pat. Pub. 2009/0209626, published Aug. 20, 2009, the entire disclosures of which are both incorporated by reference as if set forth fully herein. These modifications may include one or more sense strand modifications and/or one or more antisense strand modifications. The sense strand modifications may for example be one or more of 2'-O-methyl modifications on nucleotides 1 and 2 (counting from the 5' end of the strand), 2'-O-methyl modifications on all Cs and Us and cholesterol conjugated to the 3' terminus using a C5 linker. The antisense strand modifications may be one or more of a 5' phosphate, 2' F on all Cs and Us, a two nucleotide (UU) overhang on the 3' terminus and phosphorothioate internucleotide modifications between the two nucleotides of the overhang and between the first (3' most) nucleotide of the duplex and the first nucleotide of the overhang. By convention, when referring to RNA unmodified nucleotides are presumed to have OH groups at their 2' positions.

In addition, mismatches at positions 6, 13, and 19 of the sense strand may be incorporated into molecules. In all cases, mismatches between the two strands of the siRNA are achieved by changing the nucleotide of the sense strand to have identity with the base (on the antisense strand) that typically pairs with that position. Thus, for instance, if the sense-antisense pair at sense strand position 6 is normally U-A, then the mismatch will be introduced by converting the pair to A-A. Similarly, if the sense-antisense pair at sense strand position 6 is G-C, then the mismatch will be C-C. In this way, a mismatch is incorporated into the duplex, but the antisense strand remains the complement of the intended target. In some embodiments, there are no mismatches.

Examples of duplexes used in connection with the present invention may contain a sense sequence that is delineated in Table I and/or an antisense sequence that is the complement of a sequence delineated in Table I. The duplexes may have none or any one or more of the aforementioned modifications, including a mismatch as described above.

TABLE I

| Gene Target | siRNA # | Sequence | Sequence ID Number |
|---|---|---|---|
| Drosha | 1 | GAAGCUCGAUGAAGAUUUA | 1 |
| Drosha | 2 | GGAAUUAUAUGACUGGAAU | 2 |
| Drosha | 3 | GCAAGACGCACAGGAAUUA | 3 |
| Drosha | 4 | CAACAUAGACUACACGAUU | 4 |
| DICER | 1 | UAAAGUAGCUGGAAUGAUG | 5 |
| DICER | 2 | GGAAGAGGCUGACUAUGAA | 6 |
| DICER | 3 | GAAUAUCGAUCCUAUGUUC | 7 |
| DICER | 4 | GAUCCUAUGUUCAAUCUAA | 8 |

TABLE I-continued

| Gene Target | siRNA # | Sequence | Sequence ID Number |
|---|---|---|---|
| DGCR8 | 1 | GAAAGAAGCCCAAGAUGUC | 9 |
| DGCR8 | 2 | GCUUAAGGAUGUAAAGAUU | 10 |
| DGCR8 | 3 | UGACACGUCUAUCAAGUUU | 11 |
| DGCR8 | 4 | GCAGUUAGCCUCACAGAAG | 12 |
| Hrs | 1 | GCACGUCUUUCCAGAAUUC | 13 |
| Hrs | 2 | AGAGAGCGAUGCCAUGUUU | 14 |
| Hrs | 3 | GAUAUUCUGUGGAAAGUGU | 15 |
| Hrs | 4 | GUAAACGUCCGUAACAAGA | 16 |
| Tetherin | 1 | GGAGAGAUCACUACAUUAA | 17 |
| Tetherin | 2 | GCAGAGUGCCCAUGGAAGA | 18 |
| Tetherin | 3 | GAAUCGCGGACAAGAAGUA | 19 |
| Tetherin | 4 | GGAUAGGAAUUCUGGUGCU | 20 |

Multiple different technologies can also be used to enhance or up-regulate gene function. These can be used alone or in combination and include but are not limited to: (1) enhancing transcription by e.g., epigenetic means or by modulating gene copy number; (2) enhancing gene translation (e.g., by limiting translation attenuation or transcript degradation by miRNAs); and/or (3) modulating protein function by any number of means including but not limited to creating a constitutively active form of the protein or "evolving" protein function by in vitro mechanisms, altering post-translational modification patterns that regulate protein function (e.g., elimination of phosphorylation sites), or enhancing protein function using e.g., small molecules or peptides. In one preferred method, gene function is enhanced using over-expression constructs. Over-expression of a desired protein can be achieved by a number of means including, but not limited to introduction of an expression construct (e.g., a plasmid or viral construct) comprising a constitutive or regulated promoter sequence operationally linked to an ORF or cDNA sequence. Additionally, one may develop stable cell lines that, for instance, exhibit enhanced or up-regulated function of a desired gene.

Host genes identified by the invention can be suppressed singularly, or in combination with other gene functions that are suppressed, and/or in combination with still other gene functions that are enhanced or up-regulated. Examples of host genes that can be suppressed include, but are not limited to, Dicer, Drosha, DGCR8, Hrs, Tetherin, CDK13, TRIM-5alpha, PRMT6, as well as miR-29a, b, and c. Similarly, host-encoded gene functions can be enhanced/up-regulated singularly, in combination with other gene functions that are enhanced or up-regulated, and/or in combination with gene functions that are suppressed. Examples of host genes that can be enhanced include, but are not limited to, Annexin2, Tsg101, DBR1, RNA Helicase A, SOCS1, Cyclophillin A and TRBP.

The reagents and processes of the invention can be applied to enhance the production of a number of viruses including but not limited to a wide range of lentiviruses as well as retroviruses. As such, the invention has utility in multiple fields including those associated with industry and therapeutics. In industry, the invention can be used to greatly enhance the production of e.g., lentiviral particles carrying e.g., cDNA, ORF, or shRNA payloads, thereby reducing the costs associated with production of these important reagents for academic, industrial, and governmental researchers. Similarly, in therapeutics, the invention can be used to greatly enhance the production of lentiviral particles carrying cDNAs, ORFs, and/or shRNAs used in the treatment of both human and non-human diseases. Alternatively, the invention can be used to greatly enhance the production of e.g., lentiviral particles used in e.g., vaccines for HIV, FIV, and other lenti- or retroviruses.

As noted above, suppression of genes that inhibit lentiviral titers may be complete or partial. For example, suppression may be from 10% (90% expression) to 100% (complete suppression) relative to a normal expression, or from 5% to 10% suppression, or from 10% to 20% suppression, or from 30% to 40% suppression, or from 40% to 50% suppression, or from 50% to 60% suppression, or from 60% to 70% suppression, or from 70% to 80% suppression, or from 80% to 90% suppression. Similarly, enhancement of genes that facilitate expression of lentiviral titers may be designed to enhance expression by greater than 5%, greater than 10%, greater than 20%, greater than 30%, greater than 40%, greater than 50%, greater than 60%, greater than 70%, greater than 80%, greater than 100%, greater than 150% or greater than 200%.

When carrying out the methods of the present invention one may first select a cell type or cell line that is compatible with 1) standard transfection procedures (lipid- or calcium phosphate mediated), and 2) the replication, packaging, and release of lentiviral viruses. Examples of cell lines that would be compatible with the invention include, for instance, HEK 293T cells.

In addition to selecting a cell line, it is necessary to select the necessary genetic elements (plasmids, vectors) needed to generate a lentiviral particle. Both the number of functions (and therefore the number of vectors/plasmids) required to generate a lentiviral particle can vary. In one preferred method, the materials would include a lentiviral transfer vector/plasmid that contains the necessary genetic elements 1) to be packaged into a lentiviral particle, and 2) to infect a target cell. For example, the transfer vector may include a 5' and 3' LTR, a cPPT site, and a Psi site. In addition, the materials would include one or more accessory packaging plasmids that provide additional functions needed for packaging e.g., the transfer vector/plasmid into a viral particle. Functions encoded by the one or more packaging plasmids may include an envelope protein (env) expression cassette and a polymerase protein expression cassette. It should be noted that while the necessary functions described above are delivered to cells via plasmid or vector expression constructs, it is also possible that a transgenic cell line can be generated that expresses one or more of the needed functions in the packaging cell line in a constitutive or regulated fashion.

In order to generate a lentiviral preparation of high titer, one would begin by plating the cell line described above in e.g. a tissue culture plate with the appropriate media. After a sufficient period of time (e.g., overnight), the researcher may introduce an siRNA sequence (or sequences) into the cells or cause one or more siRNA or shRNA sequences to be generated in the cell by a vector that is introduced or already present. Alternatively, the researcher may treat the cell with a reagent (e.g., a small molecule, an antisense molecule) that, like the siRNA, targets the gene of interest. Following a period of incubation that is sufficient for the agent (e.g., siRNA) to knockdown or inhibit the target gene of interest, the cells would be transfected with the previously described genetic elements (plasmids, vectors) needed to generate a lentiviral particle. Methods for introducing a plasmid or plasmids into cells are well recognized in the art and include electroporation, lipid-mediated transfection, and more. Following this procedure, cells would be cultured using standard tissue culture practices. At an appropriate period of time (generally 24-96 hrs post-transfection) the culture supernatant containing the high titer virus can be collected and used immediately.

EXAMPLES

Example I

Effects of Knockdown of Genes Associated with the RNAi Pathway on Lentiviral Titer To determine the effects of the RNAi pathway on lentiviral titer, HEK 293T cells (ATCC) were first seeded ($6 \times 10^5$ cells/well, 6 well plate) and cultured for 18-24 hours. Subsequently, a pool of siRNAs (SMARTpools, Thermo Fisher Scientific, Dharmacon Products) targeting 1) Dicer (cat. no. M-003483-00-0005), 2) Drosha (cat. no. M-016996-02-0005), or 3) DGCR8 (cat. no. M-015713-01-0005) were transfected (25 nM) into the cells by lipid mediated transfection (DharmaFECT 1, Thermo Fisher Scientific, Dharmacon Products) using manufacturer's recommended procedures. The pools of siRNA were duplexes that contained sense strands that contained the sequences identified in Table I.

Twenty-four hours post-transfection (Day 3) cells were co-transfected with a pool of plasmids that included a lentiviral transfer vector (6 micrograms/well) and accessory packaging vectors (TransLenti Packaging Mix, Thermo Fisher Scientific, Open Biosystems Products) using calcium phosphate precipitation. Cell culture media was replaced 18 hours post-transfection and viral supernatants were collected 48 hours later. Viral titer was then determined by transduction, which involved infecting 293T cells with dilutions of the viral supernatant and measuring the number of cells expressing the viral-associated GFP reporter vector. All experiments were done in triplicate and results were normalized to a non-targeting control siRNA (NTC cat. no. D-001210-01-05, Thermo Fisher Scientific, Dharmacon Products).

Figure 2:
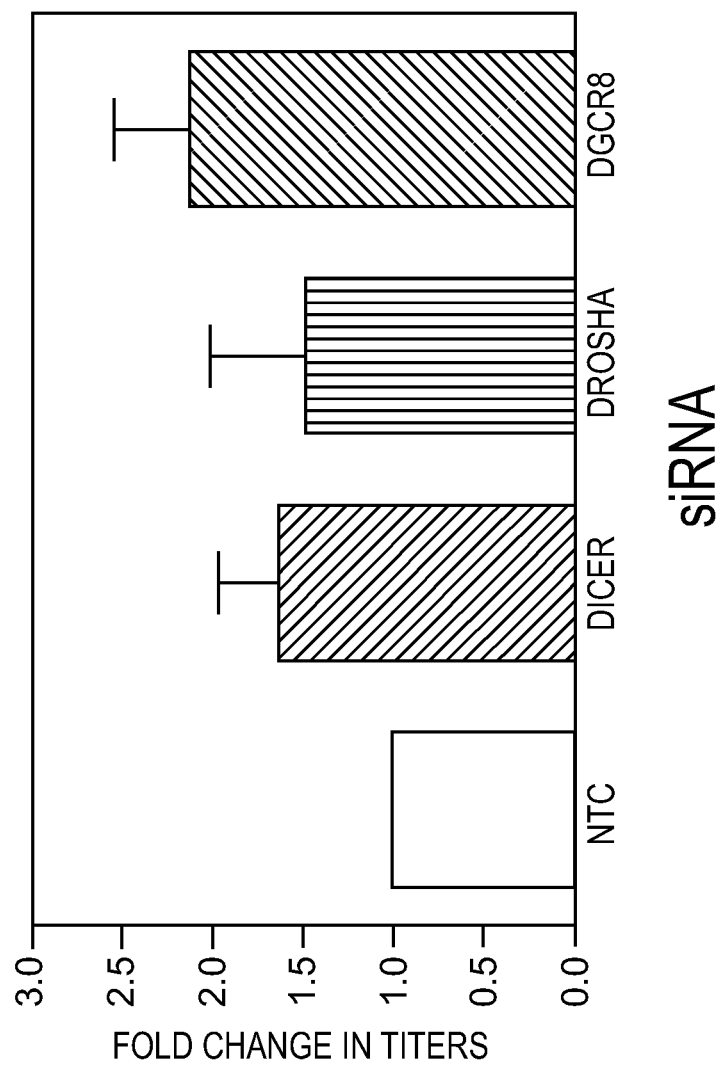
FIG. 2 is a graph showing the effects of each of Dicer, Drosha, and DGCR8 knockdown on lentiviral titers. NTC represents a non-targeting control.

The results of these studies are shown in FIG. 2. All three knockdowns were successful. The siRNA-mediated knockdown of Drosha enhanced overall viral titer by about 1.5 times. RNA mediated knockdown of Dicer enhanced overall titers by over 1.5 times while RNAi mediated the knockdown of DGCR8 increased titers by over two-fold.

Figure 3:
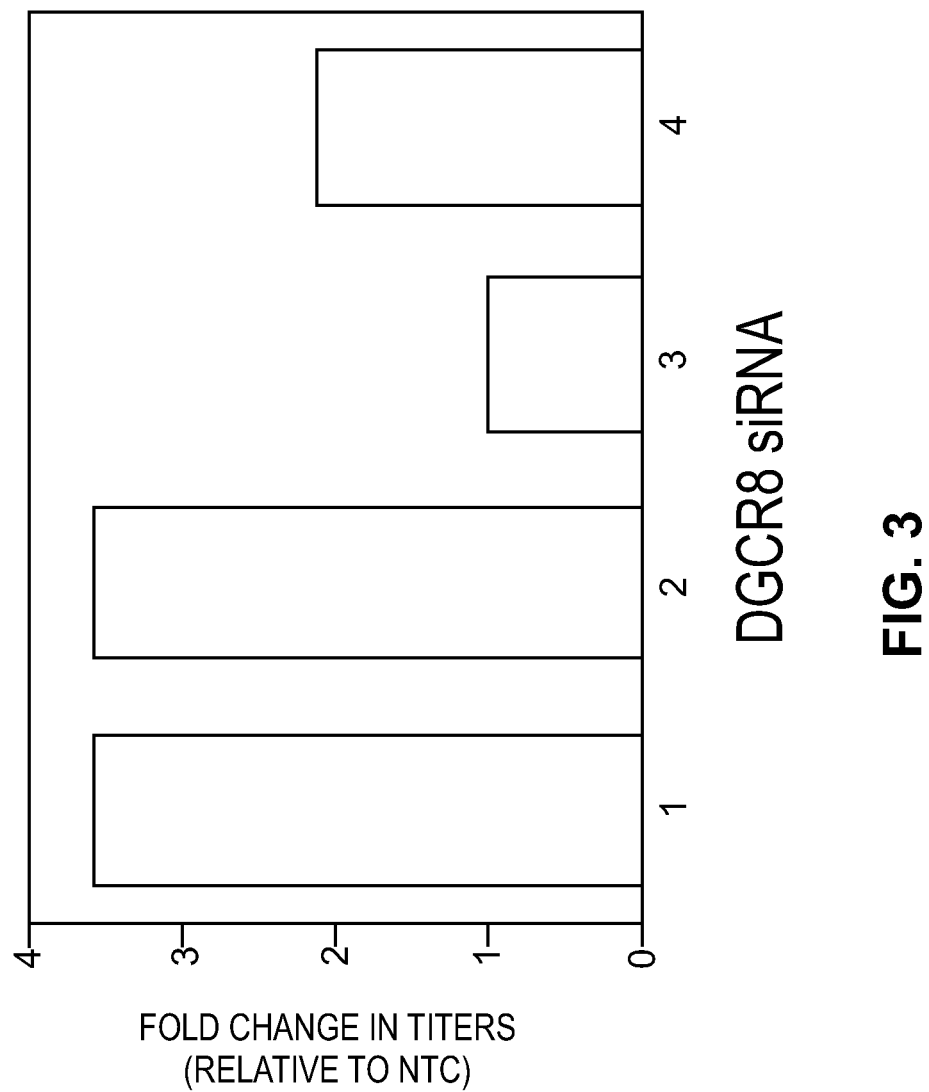
FIG. 3 is a graph showing the effects that four separate siRNAs targeting DGCR8 have on LV titer.

As a follow up to these experiments, the researchers assessed whether all of the siRNA in the pool of four siRNAs performed equivalently. Protocols were identical to those described previously with the exception that individual siRNA were introduced into cells at concentrations of 25 nM rather than pools. All experiments were performed in duplicate. As shown in FIG. 3, three out of the four siRNA present in the original pool increased viral titers. While siRNA duplex #3 failed to affect overall titers, duplex #4 increased titers by roughly two-fold while duplexes #1 and #2 increased viral titer by 3.5-4 fold. Demonstration that multiple siRNA induce similar phenotypes validates DGCR8 as a host-encoded target that (when silenced) greatly enhances lentiviral titers.

Figure 4:
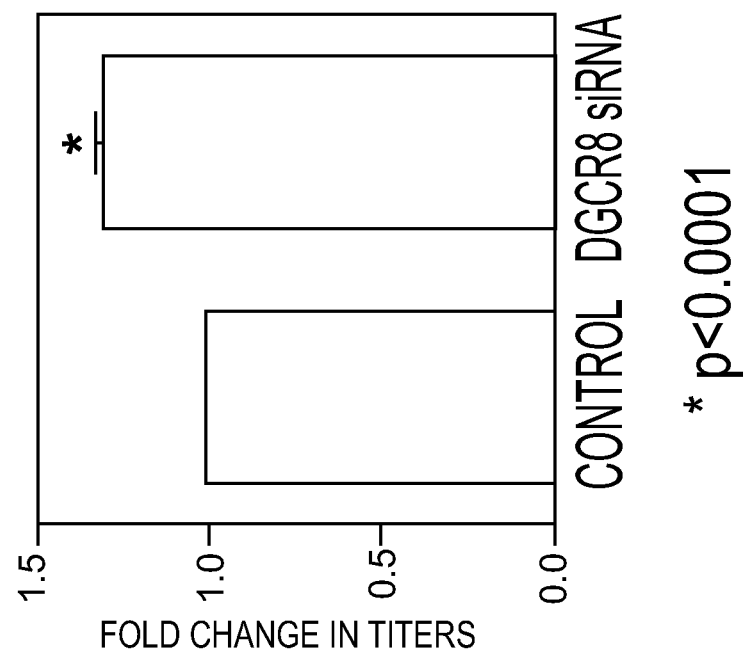
FIG. 4 is a graph showing the effects of DGCR8 knockdown on LV titers when the siRNA, packaging vectors, and transfer vector, are simultaneously introduced into cells.

In a separate experiment, the inventors tested whether simultaneous transfection of DGCR8 siRNA together with 1) LV transfer vectors, and 2) LV packaging vectors led to an increase in lentiviral titers. As was the case in previous experiments, packaging cells were seeded and cultured overnight. On Day 2, the pools of siRNA targeting DGCR8 were co-transfected into cells along with the LV transfer and packaging vectors using calcium phosphate precipitation. Three days post-transfection (Day 5), viral supernatants were collected and titers were determined as previously described. As shown in FIG. 4, simultaneous introduction of the DGCR8 siRNAs along with the packaging mixture provided significant increases in viral titer.

Example II

Effects of Knockdown of Hrs and Tetherin on Lentiviral Titers

Figure 5:
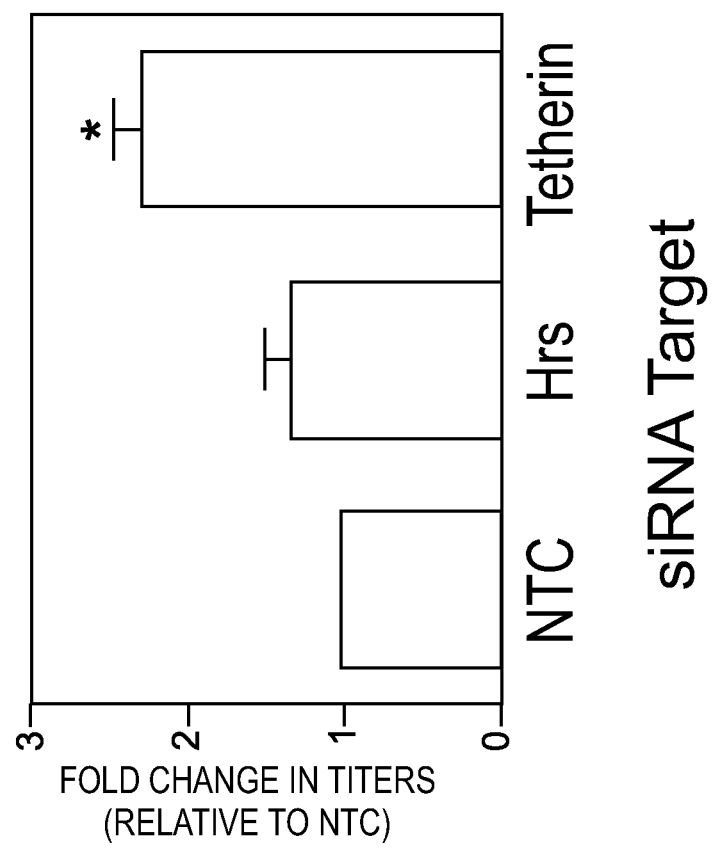
FIG. 5 is a graph showing the effects that knockdown of Hrs or Tetherin have on LV titers.

Using the original protocol, the researchers investigated the effects that siRNA-mediated knockdown (KD) of Hrs and Tetherin (Thermo Fisher Scientific, Dharmacon Products, cat. no. M-011817-00-0005 (Tetherin) and M-016835-00-0005 (Hrs)) would have on lentiviral titers. As shown in FIG. 5, KD of Hrs provided only modest increases in viral titers (<1.5× effects). In contrast, KD of Tetherin induced significant increases in viral titer (greater than two fold, $p<0.05$).

Example III

Effects of Over-expression of Annexin2 and Tsg101 on Lentiviral Titers

To test the effects that over-expression of Annexin2 has on lentiviral titers, lentiviral particles capable of expressing the Annexin2 or Tsg101 open reading frame (ORF) were transduced into HEK293T cells at an MOI of either 0.3 or 3.0 (LentiORF, Thermo Fisher Scientific, Open Biosystems Products cat. no. PLOHS_100003638 (Annexin 2) and PLOHS_100005422 (Tsg101)). Subsequently, cultures were grown in the presence of blasticidin (10 ug/ml, 2 week) to select for stable integrants. Cells were then expanded for 1 week in the absence of blasticidin, seeded at a density of $1.2 \times 10^6$ cells per well in a 6 well plate, and then transfected with a transfer vector/Trans-Lenti packaging mixture (available from Thermo Scientific).

Figure 6:
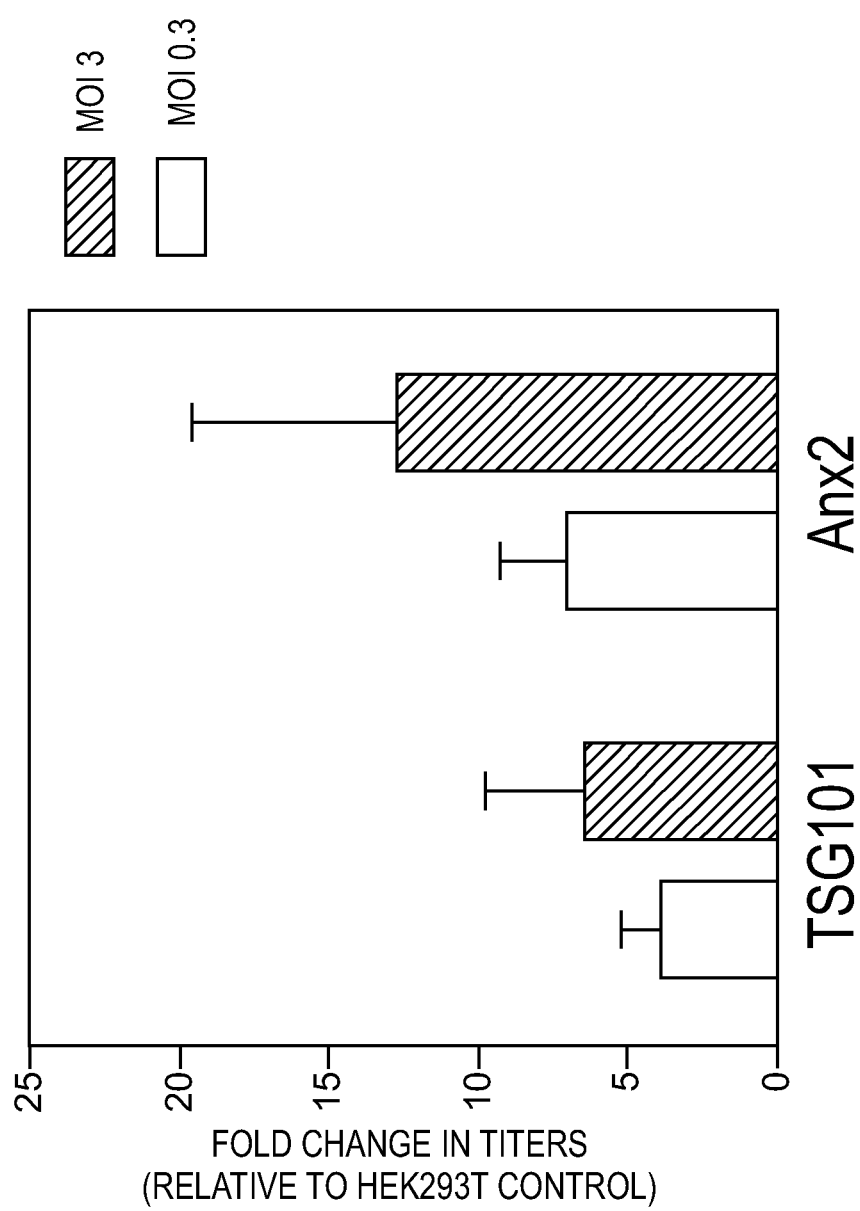
FIG. 6 is a graph showing the effects that over-expression of Tsg101 or Annexin2 (Anx2) have on LV titers. MOI=multiplicity of infection.

The results of these studies are shown in FIG. 6 which shows that over-expression of TSG101, as well as Annexin 2 increase in viral titers.

The studies described above have identified multiple host-encoded genes that when modulated individually (down- or up-regulated) can have significant effects on lentiviral vector particle production. Accordingly, based on the work of the inventors and described herein it is predicted that modulating a set of genes (particularly a combination of genes with different functions, e.g. a gene involved in RNAi pathway and another gene involved in viral packaging) simultaneously will yield even higher LV titers than modulating any individual gene. Thus, for example, knockdown of DGCR8 could be accompanied by knockdown of Hrs or Tetherin, or over-expression of Tsg101 or Annexin2. Alternatively, knockdown of Hrs could be accompanied by knockdown of Tetherin or over-expression of Tsg101 or Annexin 2. In yet a further permutation, down-regulation of Tetherin could be paired with over-expression of Tsg101 or Annexin2. In still another permutation, over-expression of Tsg101 could be paired with over-expression of Annexin2.

Further, additional increases in LV titers can be achieved by modulating three or more genes simultaneously. Thus, for example, three separate genes, DGCR8, Hrs, and Tetherin, could be knocked-down simultaneously to further enhance viral titers. Alternatively, other combinations of the genes (e.g., DGCR8+Hrs+Anx2) identified by these studies could be modulated simultaneously to further enhance LV production. Lastly, all of the genes identified in these studies can be modulated simultaneously to enhance LV production. Stable cell lines can be generated with any of the aforementioned modulating genes.

We claim:

1. A method of enhancing lentiviral titers comprising modulating expression of a plurality of host genes in a packaging cell, wherein the modulation comprises"
   a) suppressing expression of Tetherin, and
   b) at least one of
      i) suppressing expression of at least one of Dicer and DGCR8, and
      ii) increasing expression of at least one of TSG101 and Anx2.

2. The method of claim 1, wherein expression of Dicer is suppressed.

3. The method of claim 1, wherein expression of DGCR8 is suppressed.

4. The method of claim 3 further comprising suppressing expression of Dicer.

5. The method of claim 1, wherein expression of TSG101 is increased.

6. The method of claim 1, wherein expression of Anx2 is increased.

7. The method of claim 6 further comprising increasing expression of TSG 101.

8. The method according to claim 1, wherein said modulating expression of Tetherin comprises only partially suppressing Tetherin.

9. The method according to claim 8, wherein the at least one gene is involved in an RNAi pathway.

10. The method according to claim 1, wherein said modulating comprises expressing a first shRNA from an expression construct within the packaging cell, wherein the first shRNA inhibits Tetherin and expressing a second shRNA from the expression construct, wherein the second shRNA inhibits DGCR8.

11. The method according to claim 10, wherein each of Tetherin and DGCR8 are only partially suppressed.

12. The method according to claim 1, wherein said modulating comprises expressing an shRNA from an expression construct within the packaging cell, wherein the shRNA inhibits Tetherin, and causing overexpression of TSG101.

13. The method according to claim 12, wherein Tetherin is only partially suppressed.

14. The method according to claim 13, wherein TSG101 is overexpressed by at least 30%.

15. The method according to claim 14, wherein Tetherin is suppressed by 30% to 40%.

16. The method according to claim 1, wherein said modulating comprises expressing an shRNA from an expression construct within the packaging cell, wherein the shRNA inhibits Tetherin, and causing overexpression of Anx2.

17. The method according to claim 16, wherein Tetherin is only partially suppressed.

18. The method according to claim 17, wherein Anx2 is overexpressed by at least 30%.

19. The method according to claim 18, wherein Tetherin is suppressed by 30% to 40%.

* * * * *